US012605531B1

(12) United States Patent
Teng et al.

(10) Patent No.:  US 12,605,531 B1
(45) Date of Patent:  Apr. 21, 2026

(54) IMPLANTABLE INTRAVENOUS PORT WITH A PASSIVE ANTI-PLUGGING MECHANISM

(71) Applicant: Yuanyin Teng, Hangzhou (CN)

(72) Inventors: Yuanyin Teng, Hangzhou (CN); Mi Zhou, Chongqing (CN); Bing Wang, Guangzhou (CN); Haoran Huang, Wenzhou (CN); Tong Wang, Storrs, CT (US); Yang Yang, Yiwu (CN); Jiahui Du, Wenzhou (CN); Benfan Lin, Linyi (CN); Zihan Zhou, Yiwu (CN); Feng Xu, Nanjing (CN)

(73) Assignee: Yuanyin Teng, Hangzhou (CN)

( * ) Notice: Subject to any disclaimer, the term of this patent is extended or adjusted under 35 U.S.C. 154(b) by 0 days.

(21) Appl. No.: 19/382,317

(22) Filed: Nov. 7, 2025

(51) Int. Cl.
*A61M 39/02* (2006.01)

(52) U.S. Cl.
CPC . *A61M 39/0208* (2013.01); *A61M 2039/0205* (2013.01); *A61M 2205/04* (2013.01); *A61M 2210/12* (2013.01)

(58) Field of Classification Search
CPC ...... A61M 39/0208; A61M 2039/0226; A61M 2039/0211; A61M 2039/0214; A61M 2039/0217; A61M 2039/0241; A61M 39/0247; A61M 2039/0285; A61B 2017/32008; A61B 2017/320775; A61B 2018/00202
See application file for complete search history.

(56) References Cited

U.S. PATENT DOCUMENTS

| | | | | | |
|---|---|---|---|---|---|
| 4,364,395 | A | * | 12/1982 | Redmond | A61M 27/006 604/10 |
| 4,560,375 | A | * | 12/1985 | Schulte | A61M 39/0208 604/9 |
| 4,725,207 | A | * | 2/1988 | Buchwald | A61M 27/002 417/420 |
| 5,695,490 | A | * | 12/1997 | Flaherty | A61M 39/0208 604/288.02 |
| 7,833,204 | B2 | * | 11/2010 | Picha | A61B 17/3472 606/92 |
| 8,870,809 | B2 | * | 10/2014 | Miethke | A61M 27/006 604/9 |
| 9,416,344 | B2 | * | 8/2016 | Lipkens | B01D 17/06 |
| 9,480,831 | B2 | * | 11/2016 | Tallarida | A61M 5/158 |
| 12,440,272 | B2 | * | 10/2025 | Schmitt | A61B 17/22012 |

FOREIGN PATENT DOCUMENTS

| | | |
|---|---|---|
| CN | 112739407 A | 4/2021 |
| CN | 117462791 A | 1/2024 |
| CN | 221105831 U | 6/2024 |

* cited by examiner

*Primary Examiner* — Quynh-Nhu H. Vu
(74) *Attorney, Agent, or Firm* — Nitin Kaushik

(57) ABSTRACT
Disclosed is an implantable intravenous port with a passive anti-plugging mechanism, which comprises a port body defining a reservoir chamber and a communicating catheter connector, and an anti-plugging mechanism within the chamber, which includes a movable component that moves in response to gravity, a stirring component connected to the movable component and extending near the connector, and a damping component, wherein the damping component has a fixed bush on the chamber's inner wall forming an air chamber, and a compression component slidable within the air chamber, with the bush wall featuring a through hole communicating with both sides of the air chamber.

10 Claims, 10 Drawing Sheets

100

321 (32)

221 (22)

222 (22)

A 2221 (222)

211 (21)

100

100

13

11(1)

IMPLANTABLE INTRAVENOUS PORT WITH A PASSIVE ANTI-PLUGGING MECHANISM

TECHNICAL FIELD

This application relates to the field of medical devices, and specifically relates to an implantable intravenous port with a passive anti-plugging mechanism.

BACKGROUND

A Totally Implantable Venous Access Port (TIVAP) is an important long-term intravenous drug delivery tool in modern clinical medicine, widely used especially in areas such as cancer chemotherapy and long-term nutritional support. Its basic structure comprises an injection base (i.e., the port body) implanted under the patient's skin, and a flexible catheter. The port body internally forms a reservoir chamber for temporarily storing the medicinal liquid. The liquid is injected into the reservoir chamber by puncturing a silicone film on the top of the port body, then enters and flows through the catheter via a key structure on the sidewall of the port body-a catheter connector, ultimately being delivered to the patient's central vein, thereby establishing a semi-permanent intravenous access. This design greatly reduces the pain caused by repeated venipuncture for patients, protects peripheral blood vessels, and improves the patient's quality of life.

However, during long-term use, port blockage is a persistent clinical challenge, and the root of this problem lies precisely at the catheter connector. Chemotherapy drugs often have high viscosity. After infusion, despite standard flushing and positive pressure sealing procedures, due to the limitations of the fluid dynamics inside the reservoir chamber of existing ports, drug molecules still have a high probability of remaining near the catheter connector. Over time, these residual drug molecules gradually precipitate, gather, and form crystals on the inner wall of the catheter connector, much like scale in a water pipe, eventually leading to complete or partial catheter blockage.

Catheter blockage brings a series of serious consequences: firstly, greater pressure is required to infuse drugs, which not only increases operational difficulty but also significantly raises the risk of drug extravasation (where the drug leaks from the blood vessel into surrounding tissues), potentially causing severe tissue damage or even necrosis. Secondly, blockage affects the flow rate of drug infusion, potentially leading to inaccurate dosing. In severe cases, a blocked port must be cleared through interventional surgery or even completely replaced via a second operation, undoubtedly imposing additional trauma, infection risk, and financial burden on patients already under tremendous physical and mental stress.

Current attempts to improve this issue by optimizing flushing procedures (such as pulsed flushing) highly depend on the operator's skill and standardization, making stable results difficult to guarantee. Furthermore, patients resting at home constantly change their body postures in daily life, such as stooping, arising, and side-lying. These macroscopic body movements undoubtedly cause liquid sloshing inside the implanted port body. However, the internal structure of existing ports is entirely static; it cannot utilize this ubiquitous, free energy source—namely, the change in gravitational potential energy generated by the patient's own movement—to actively resist drug residue.

Thus, there is an urgent need for a novel design of an implantable intravenous port that can intelligently utilize the patient's natural body activities to fundamentally inhibit crystal formation and ensure long-term patency of the catheter.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended to limit the scope of the claimed subject matter.

An implantable intravenous port with a passive anti-plugging mechanism is provided, comprising:

a port body, wherein the port body internally forms a reservoir chamber and a catheter connector in communication with the reservoir chamber; and an anti-plugging mechanism set inside the reservoir chamber, the anti-plugging mechanism comprising a movable component, a stirring component, and a damping component;

wherein the movable component is capable of moving within the reservoir chamber in response to gravity;

wherein one end of the stirring component is connected to the movable component, and the other end extends to the vicinity of the catheter connector; and wherein the damping component comprises a fixed bush and a compression component, the fixed bush is fixedly set on an inner wall of the reservoir chamber and internally forms an air chamber, the compression component is slidably set within the air chamber, and a wall of the fixed bush is provided with a through hole, the through hole communicating with both sides of the air chamber.

The above aspects or examples and advantages, as well as other aspects or examples and advantages, will become apparent from the ensuing description and accompanying drawings.

BRIEF DESCRIPTION OF DRAWINGS

To illustrate the technical solutions according to the embodiments of the present disclosure or in the prior art more clearly, the accompanying drawings for describing the embodiments or the prior art are introduced briefly in the following. Apparently, the accompanying drawings in the following description are only some embodiments of the present disclosure, and persons of ordinary skill in the art can derive other drawings from the accompanying drawings without creative efforts.

REFERENCE NUMBERS

Figure 1:
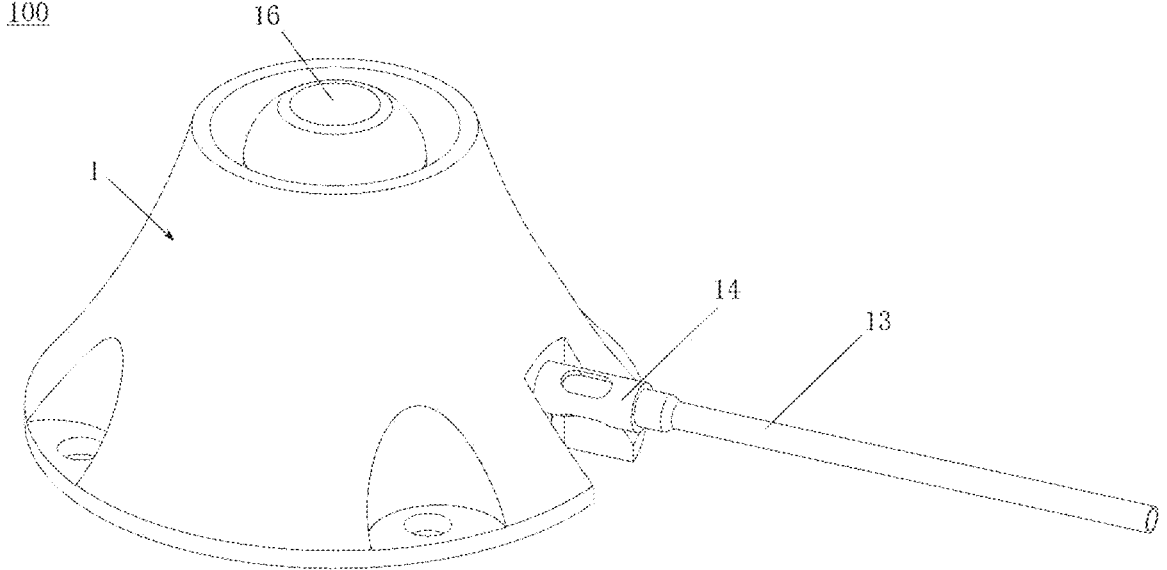
FIG. 1 is a schematic diagram of the overall structure of an implantable intravenous port according to an embodiment of the present application.

100: implantable intravenous port
1: port body; 11: housing; 12: reservoir chamber; 13: catheter; 14: positioning sheath; 15: catheter connector; 151: near-end opening; 16: silicone film
2: anti-plugging mechanism; 21: movable component; 211: slidable ring; 22: stirring component; 221: stirring rod; 222: inclined panel; 2221: first sealing ring; 23: damping component; 231: fixed bush; 232: compression component; 233: air chamber; 234: connecting plate; 235: through hole
3: pushing mechanism; 31: displacement component; 311: displacement ring; 32: grid plate; 321: grid strip; 33: stopping structure; 34: second sealing ring; 35: connecting rod.

DETAILED DESCRIPTION OF THE EMBODIMENTS

The present disclosure will be further described in detail below with reference to the drawings. A preferred embodiment is described in the drawings. However, the present disclosure can be implemented in many different forms and is not limited to the embodiments described herein. Rather, these embodiments are provided to provide a thorough understanding of the present disclosure. The specific embodiments are only explanations of the present disclosure, and the embodiments are not intended to limit the present disclosure. Rather, various modifications may be made in the details within the scope and range of equivalents of the claims and without departing from the present disclosure.

The present disclosure will be described in more details below with reference to the accompanying drawings and in conjunction with embodiments. The examples are provided for better illustration of the present disclosure and should not limit the scope of the present disclosure. In practice, technicians skilled in the art might make small modifications and/or variations of the present disclosure without departing from the scope or spirit of the present disclosure. For example, features described in part of one embodiment may be used in another to create a new embodiment. It is therefore desirable that the present disclosure encompass such modifications and/or variations falling within the scope of the appended claims and their equivalents.

In the description of the present disclosure, terms like "longitudinal", "transverse", "up", "down", "front", "back", "left", "right", "vertical", "horizontal", "top", "bottom" denote orientation or positional relationships based on those shown in the drawings and are intended for ease of description only, which in no way entails that the present disclosure must be constructed and operated in a particular orientation and therefore cannot be construed as limiting to the present disclosure. Terms like "joint", "attach" and "set" used in the present disclosure should be understood in a broad sense, for example, may indicate a direct connection or indirect connection through intermediate components; and it may be a wired electrical connection, a radio connection, or a wireless communication signal connection. The exact meanings of the above terms may slightly differ and should be derived from the actual situation by technicians skilled in the art accordingly.

Figure 2:
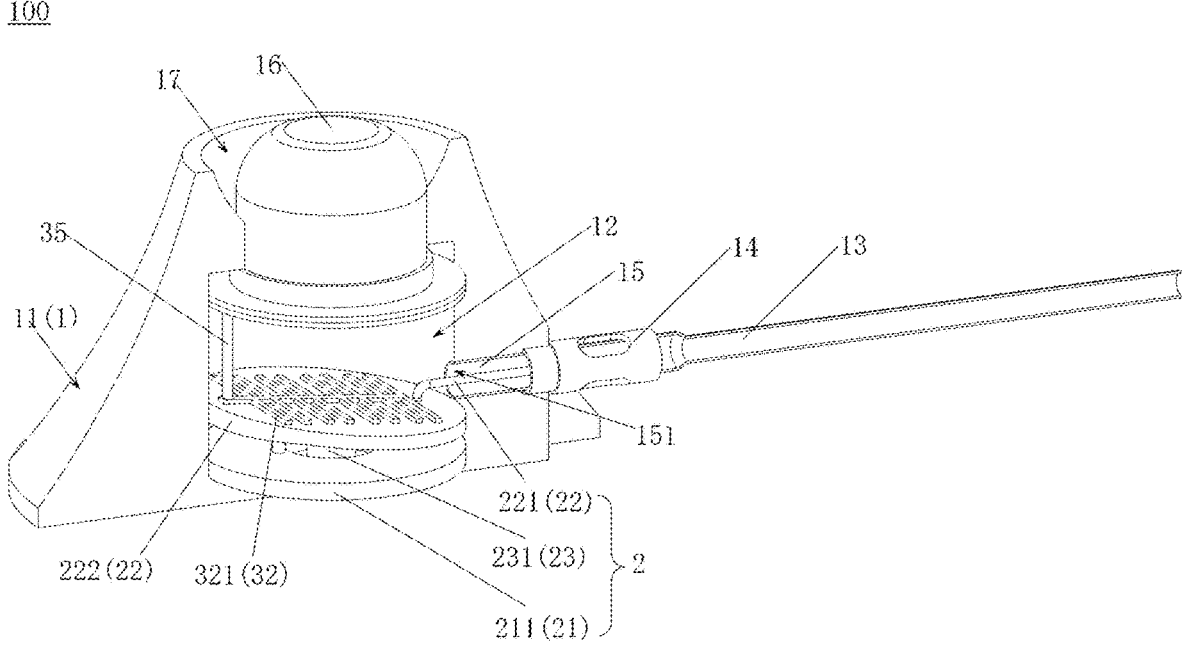
FIG. 2 is a cross-sectional view of the implantable intravenous port shown in FIG. 1.
Figure 3:
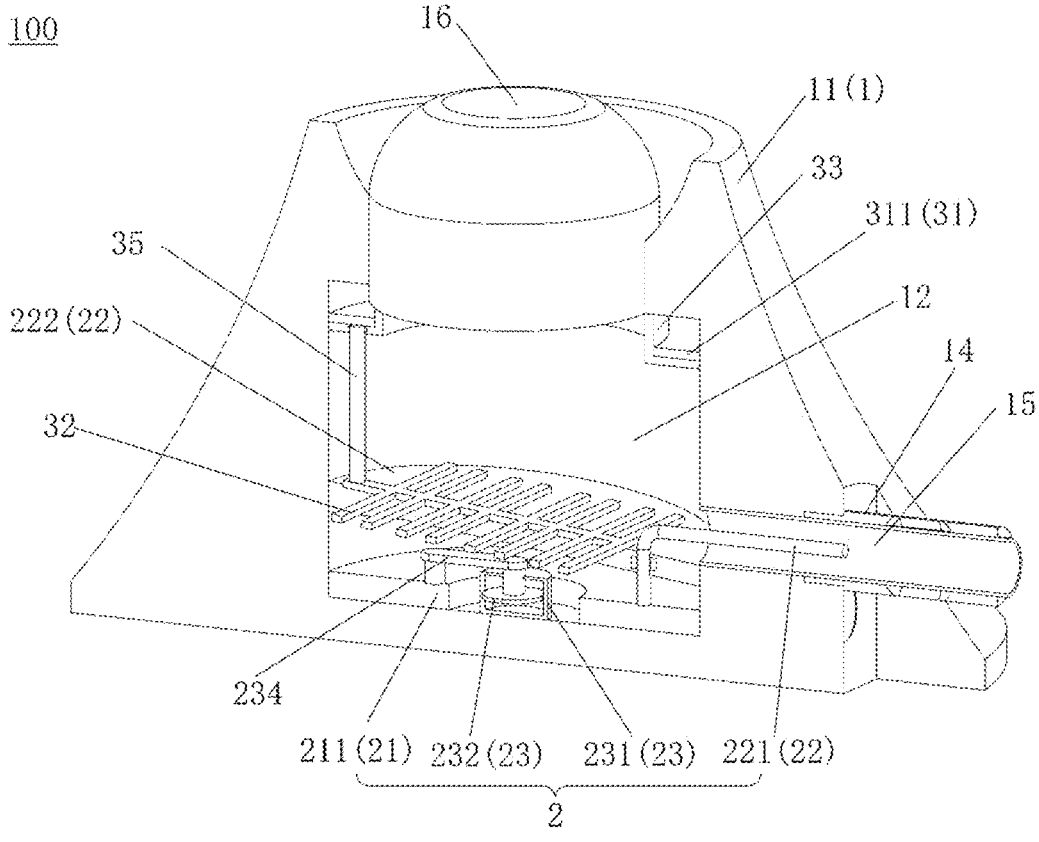
FIG. 3 is another cross-sectional view of the implantable intravenous port shown in FIG. 1 from a different perspective.
Figure 4:
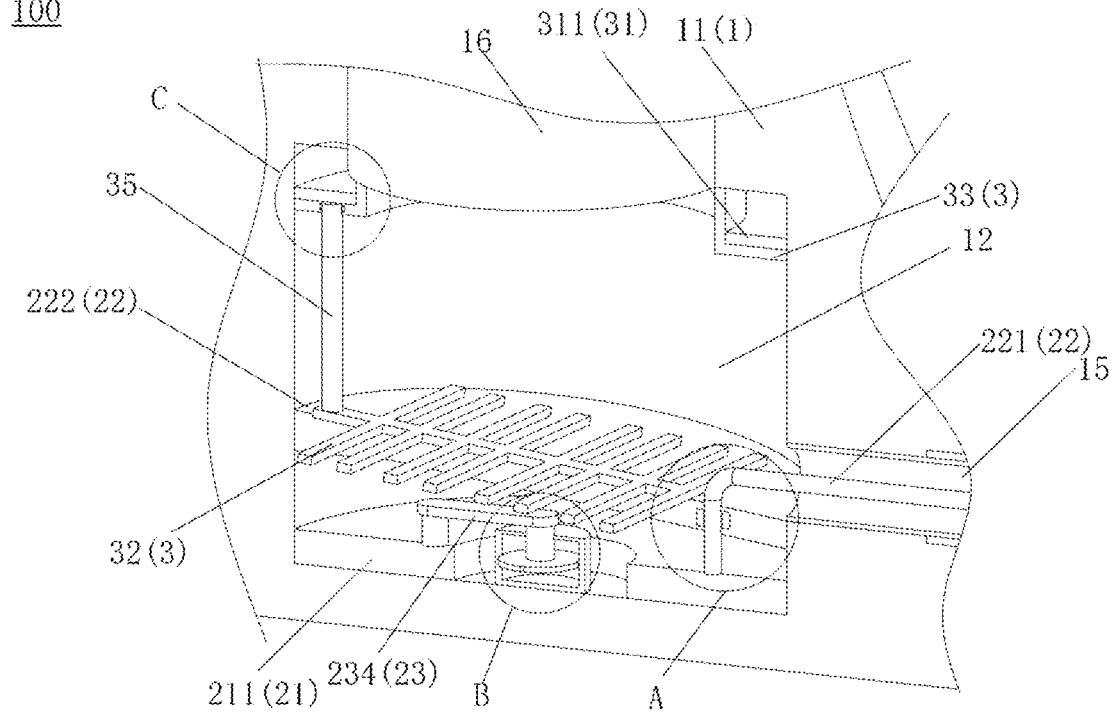
FIG. 4 is a partial enlarged view of a structure in FIG. 3.
Figure 5:
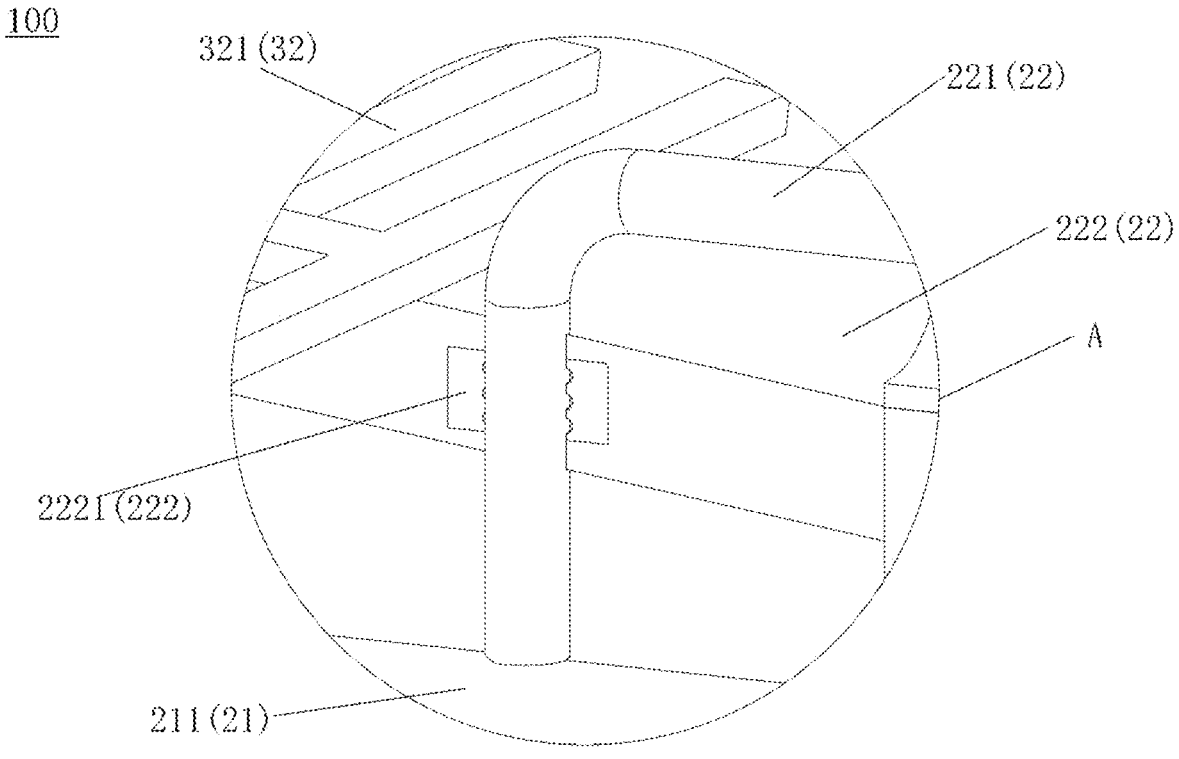
FIG. 5 is a partial enlarged view of part A in FIG. 4.
Figure 6:
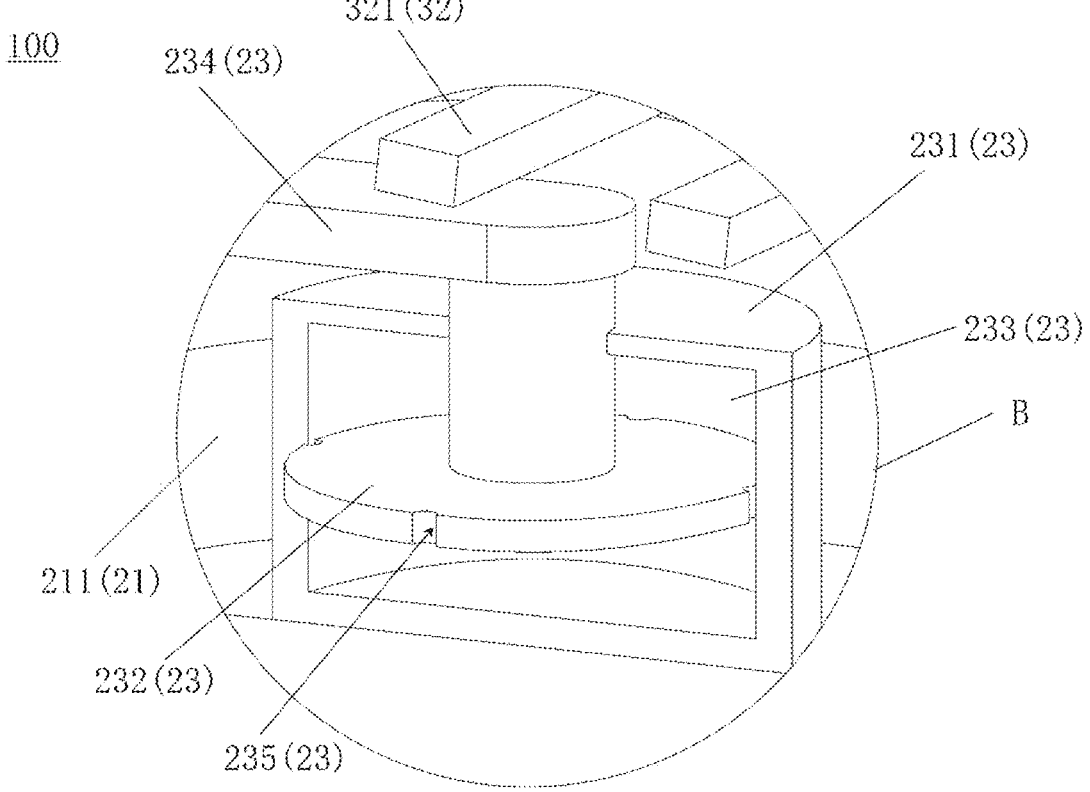
FIG. 6 is a partial enlarged view of part B in FIG. 4.
Figure 7:
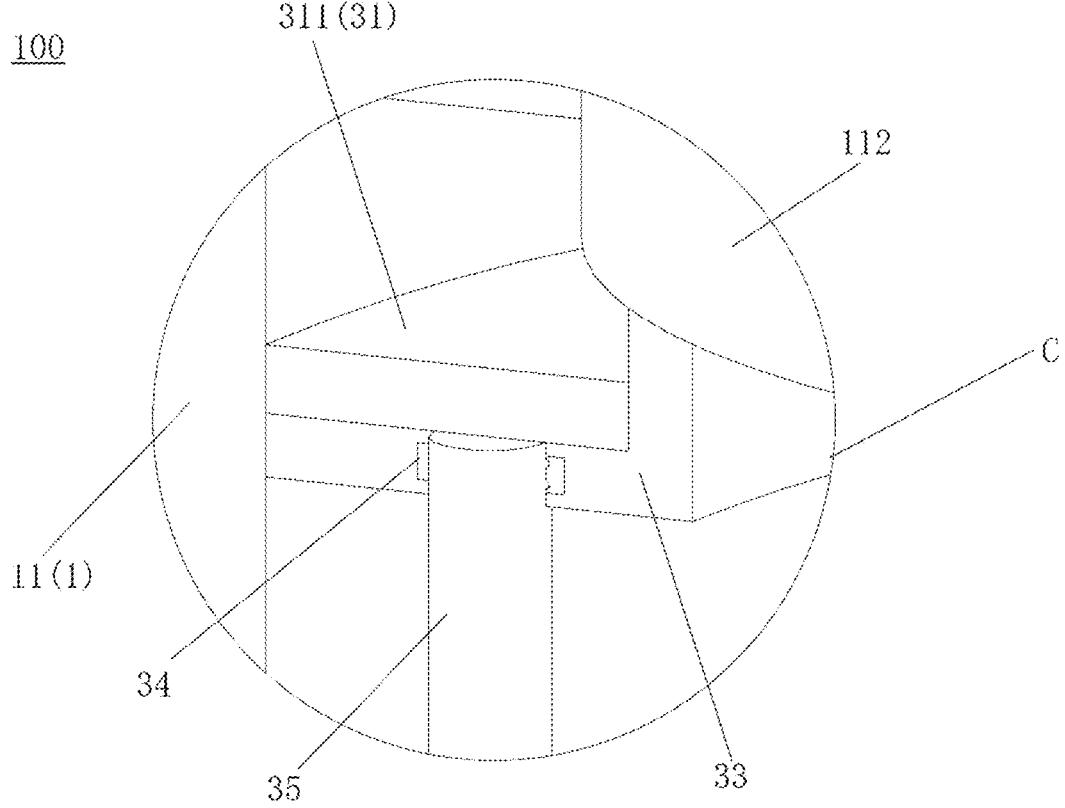
FIG. 7 is a partial enlarged view of part C in FIG. 4.
Figure 8:
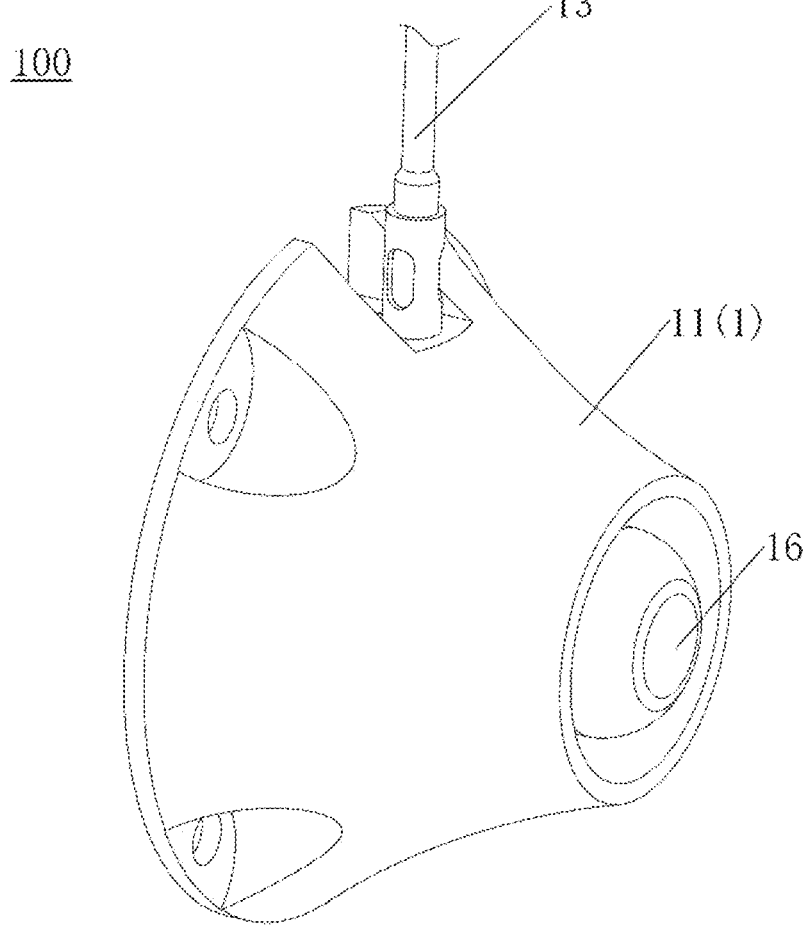
FIG. 8 is a schematic diagram of the overall structure of the implantable intravenous port shown in FIG. 1 from another angle.
Figure 9:
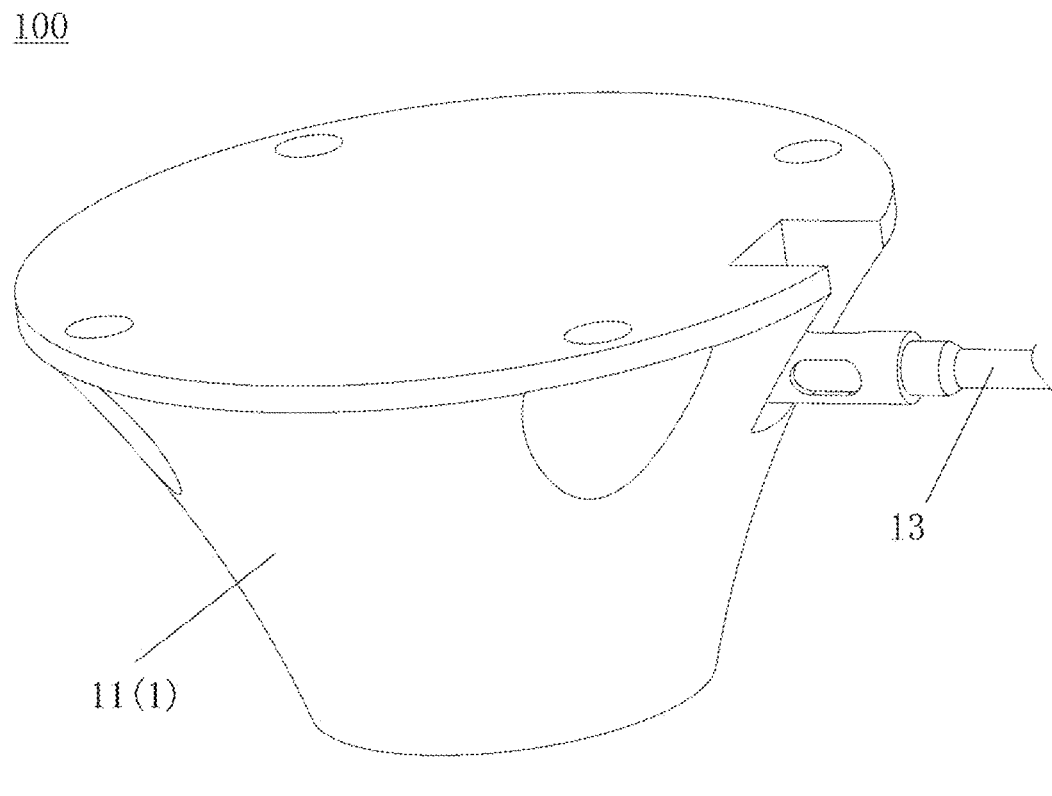
FIG. 9 is a schematic diagram of the overall structure of the implantable intravenous port shown in FIG. 1 from another angle.
Figure 10:
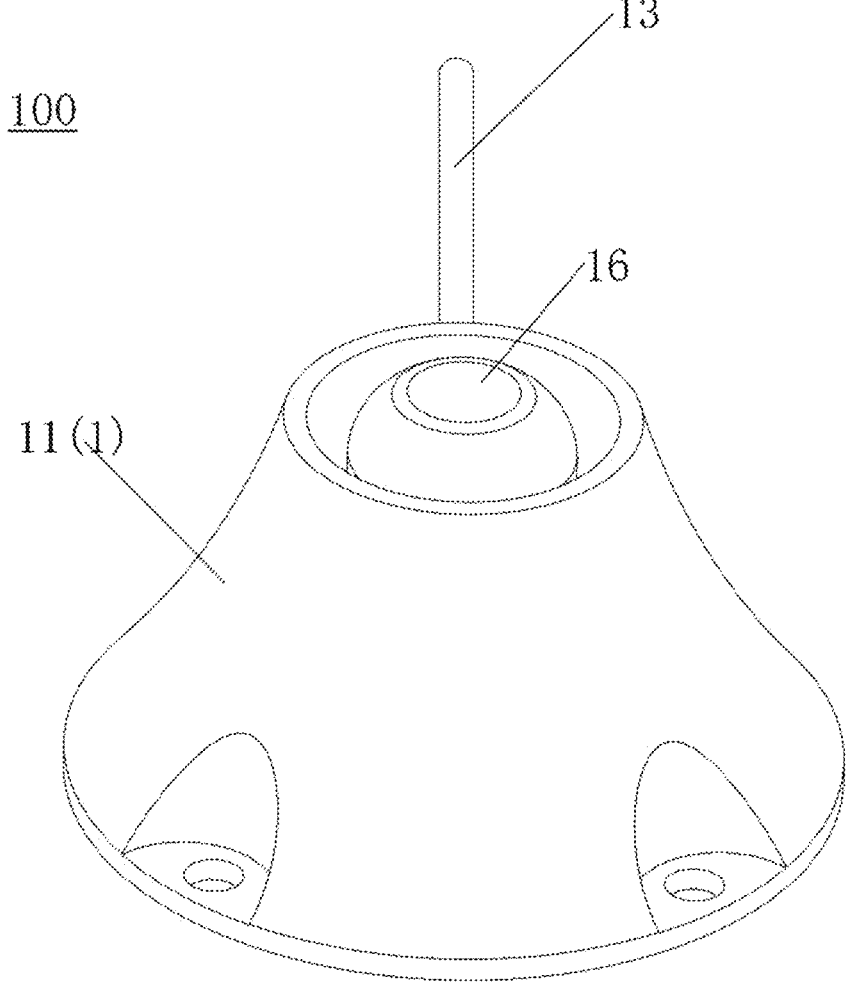
FIG. 10 is a schematic diagram of the overall structure of the implantable intravenous port shown in FIG. 1 from another angle.

Referring to FIGS. 1-10, This application provides an implantable intravenous port 100, the main function of which is: after the device is implanted in a patient, it can automatically and without external energy utilize the gravity changes generated by the patient's daily body activities to continuously and gently clean the catheter connector and the bottom of the reservoir chamber, which are most prone to drug residue crystallization, thereby actively preventing catheter blockage caused by the long-term retention and adhesion of high-viscosity drugs (such as chemotherapy drugs) from the source, to maintain the long-term patency of the catheter.

To achieve the above function, the implantable intravenous port 100 mainly includes a basic port body 1 and an anti-plugging mechanism 2 integrated therein. In some embodiments, an optional pushing mechanism 3 may also be included to achieve more comprehensive cleaning.

The port body 1, as the basic framework and housing of the entire device, constitutes the platform for realizing the basic infusion function. Its interior forms a reservoir chamber 12 for containing the drug solution, the top is provided with a silicone film 16 for puncture, and the side wall is provided with a catheter connector 15 communicating with the reservoir chamber 12. This connector is firmly connected to a catheter 13 via a positioning sheath 14.

The anti-plugging mechanism 2 is completely set within the reservoir chamber 12 of the port body 1 and is a purely mechanical, highly integrated self-cleaning system. This mechanism includes a movable component 21, a stirring component 22, and a damping component 23. These three components are closely coordinated in function and interconnected in structure.

The various components are precisely fitted in structure, and the port body 1 encapsulates and contains the anti-plugging mechanism 2 and the pushing mechanism 3. The movable component 21, the stirring component 22, and the damping component 23 of the anti-plugging mechanism 2 are mechanically linked to each other and jointly respond to gravity changes. The movable component 21 is used to sense the change in the direction of gravity caused by changes in the patient's body posture and convert it into usable mechanical displacement; the stirring component 22 is mechanically linked with the movable component 21, and its working end accurately acts on the catheter connector 15 area, stirring the liquid in this area through physical stirring, scraping, etc., to prevent high-concentration drug molecules from staying, adhering, and crystallizing for a long time; the damping component 23 is linked to the movement of the movable component 21, and through physical damping, it ensures that no matter how sudden or drastic the patient's movements are, the cleaning action of the stirring component 22 is always smooth, gentle, and controlled, thereby avoiding impact on internal structures or blood vessels and ensuring the absolute safety of the device's operation.

The pushing mechanism 3, as an optional enhanced structure for the anti-plugging mechanism 2, is used to supplement and enhance the function of the anti-plugging mechanism 2. This mechanism is also driven by gravity and is used to stir and clean other areas at the bottom of the reservoir chamber 12, complementing the precise "point" cleaning of the stirring component 22 to achieve more comprehensive "surface" cleaning, preventing drugs from depositing over a large area at the bottom.

Thus, the port body 1 provides the basic platform for drug infusion, while the anti-plugging mechanism 2, based on this platform, through the seamless cooperation of the movable component 21, the stirring component 22, and the damping component 23, transforms a static infusion container into a micro-mechanical device with dynamic self-maintenance and active blockage prevention capabilities, achieving a perfect unity of preventive maintenance, safety, and high reliability.

A. Port Body

The function of the port body 1 is to serve as the basic structure of the intravenous port, providing an interface for drug injection, containing internal functional mechanisms, and connecting the infusion catheter. It is made of biocompatible materials (such as titanium alloy or medical-grade polymer). It mainly includes a housing 11, a reservoir chamber 12, a catheter 13, a positioning sheath 14, a catheter connector 15, and a silicone film 16.

The housing 11 serves as the base and protective shell of the entire device, containing all internal components and withstanding the physical pressure and chemical effects from the implantation environment. Its external shape is designed according to ergonomics to reduce the patient's foreign body sensation and skin tension after implantation. Housing 11 is usually made of materials with high biocompatibility, corrosion resistance, and sufficient mechanical strength. Common choices include medical-grade titanium alloy, which has the advantages of high strength, good tissue compatibility, and small artifacts in magnetic resonance imaging (MRI) examinations; or medical-grade polymers, such as Polyetheretherketone (PEEK) or Polysulfone, which have the advantages of being lightweight, low-cost, and not producing artifacts in X-ray or CT imaging, which is convenient for observing surrounding tissues. The overall shape of housing 11 is usually designed to be flat with rounded edges, such as circular, oval, or triangular, with a flat or slightly curved bottom to fit the body contour. Its top has an opening for installing the silicone film 16, and the side wall is processed with a catheter connector 15 for connecting the catheter 13. Thus, housing 11, with its sturdy, stable, and inert physical and chemical properties, builds a long-term and safe "workstation" for the entire infusion system within the human body.

It is understandable that, in some embodiments, the housing 11 is designed as two or more separable modules, for example, a permanently implanted base module (containing the catheter connection system) and a percutaneously replaceable top module (containing the silicone film). When the silicone film approaches its service life due to long-term puncture, a doctor can replace only the top module through a minimally invasive surgery, without needing to replace the entire port body and catheter, greatly reducing maintenance costs and surgical trauma.

It is understandable that, in some embodiments, a passive micro pressure sensor and/or flow sensor is integrated on the inner wall of the housing 11 or at the catheter connector 15. These sensors can be queried by an external wireless reader to monitor the infusion pressure and flow rate in real time. This helps in the early detection of potential catheter blockage (manifested as increased pressure) or leakage (manifested as abnormally low pressure), achieving digital management of the infusion status.

It is understandable that, in some embodiments, the bottom of the housing 11 is provided with a plurality of suture holes for the surgeon to suture and fix it on the fascia during the implantation surgery, preventing it from shifting or flipping subcutaneously.

It is understandable that, in some embodiments, the housing 11 is made of a material with certain elasticity, such as medical-grade silicone or polyurethane. This material can better conform to human tissue, reducing the foreign body sensation after implantation and improving patient comfort.

The reservoir chamber 12 is the space inside the port body 1 used for the temporary storage of the injected drug solution. Its volume determines the maximum capacity for a single push injection or sealing liquid. The boundary of the reservoir chamber 12 is jointly enclosed by the inner wall of the housing 11 and the bottom surface of the silicone film 16. Its inner surface is designed to be smooth to reduce liquid flow resistance and lower the risk of drug crystal adhesion. The geometry of the bottom of the reservoir chamber 12 is crucial for emptying efficiency and is often designed to be tapered, bowl-shaped, or, as in the inclined panel 222 shown in this embodiment, an inclined structure, to ensure that all liquid can naturally converge to the lowest point, the catheter connector 15, under the action of gravity or fluid pressure, avoiding liquid retention. The reservoir chamber 12 acts as a temporary buffer and mixing chamber, allowing the rapidly injected drug solution from the needle to transition smoothly and then enter the catheter 13 at a controlled flow rate.

It is understandable that, in some embodiments, the interior of the port body 1 is divided into two independent reservoir chambers 12 by a vertical partition, with each reservoir chamber corresponding to an independent catheter connector and catheter. This design is suitable for scenarios requiring the simultaneous infusion of two incompatible drugs.

It is understandable that, in some embodiments, the port body 1 consists of two upper and lower parts that can move relative to each other, connected by threads or a snap-fit. By rotating the housing, the internal volume of the reservoir chamber 12 can be changed to accommodate the infusion needs of different drug doses.

It is understandable that, in some embodiments, the inner wall of the reservoir chamber 12 is surface-treated with a superhydrophobic or heparin-like coating. This surface can significantly reduce the adhesion of drug molecules and thrombi.

It is understandable that, in some embodiments, the inner wall of the reservoir chamber 12 is covered with a layer of biodegradable biomaterial, which is preloaded with anticoagulant or anti-infective drugs. In the early stage of implantation, this layer will slowly release the drugs, actively preventing thrombosis and infection.

The catheter connector 15 and the positioning sheath 14 together form a connection system that securely, reliably, and completely seals the soft, fragile catheter 13 to the hard housing 11. This is the key to ensuring the integrity of the entire infusion path and preventing fatal drug extravasation or catheter dislodgement. The catheter connector 15 is a short tube structure set on the side wall of the port body 1. The positioning sheath 14 is an independent, usually titanium alloy-made, sleeve-like locking component. The end of the catheter 13 is fitted over the catheter connector 15, and then the positioning sheath 14 is fitted over it from the outside. Through a mechanical method (such as snap-fitting, crimping, or screwing), the wall of the catheter 13 is firmly pressed onto the catheter connector 15. By means of mechanical locking, the strong radial pressure applied by the positioning sheath 14 creates an extremely strong frictional and mechanical interlock between the soft catheter wall material and the surface of the catheter connector 15, thus creating a connection that can withstand high injection pressure and long-term in vivo stress. At the same time, this compression also forms a reliable liquid-tight and gas-tight seal.

It is understandable that, in some embodiments, the catheter connector 15 is designed as a replaceable modular component. When the connector is damaged or a different type of catheter needs to be replaced, the doctor does not need to replace the entire port body 1, but only needs to replace the connector module through a simple operation.

It is understandable that, in some embodiments, two or three alternative catheter connectors 15 are provided at different angles on the side wall of the port body 1. During the implantation surgery, the doctor can choose the most suitable connector for connection based on the specific vascular path of the patient, increasing the flexibility of the surgery.

The silicone film 16 is the sole entry point for drug injection. It must allow a special non-coring needle (such as a Huber needle) to be punctured thousands of times for drug injection and be able to instantly and completely self-seal after each needle withdrawal to prevent drug leakage and bacterial invasion, maintaining the germ-free condition of the reservoir chamber 12. The silicone film 16 is made of high-density, high-resilience medical-grade silicone rubber through a special compression molding process. This material has excellent self-healing properties upon puncture and chemical inertness, able to withstand corrosion from various chemotherapy drugs. The silicone film 16 is a thick disc or plug shape, tightly embedded and fixed in the opening on top of the port body 1, with its upper surface flush or slightly convex with the upper edge of the port body, which is convenient for doctors to locate by palpation. The silicone film 16 is firmly pressed and fixed by the mechanical structure (such as an annular pressure ring or groove) at the edge of the opening of the housing 11, ensuring a high-pressure seal is formed between it and the housing 11, so that it will not be displaced or leak even under high injection pressure.

It is understandable that, in some embodiments, the film 16 can be designed with a three-layer structure: its top layer (about 70% of the thickness) uses standard soft silicone to ensure comfortable puncture; the middle layer (about 15% of the thickness) uses hard silicone, which produces a clear sense of increased resistance when the needle tip makes contact, serving as a tactile warning that the bottom is approaching; its bottom layer (about 15% of the thickness) uses a composite silicone with high tensile strength as the final physical buffer cushion, which can effectively absorb residual impact force. During the puncture process, the material will tightly "wrap and drag" the needle body, producing enormous frictional resistance to complete the final braking. Therefore, when the needle tip finally passes through the bottom layer, its speed has been greatly reduced, and the contact with the port body base changes from a high-energy "impact" to a harmless "light touch." While ensuring the needle tip completely enters the reservoir chamber, it cleverly uses the material's own physical properties to protect the integrity of the needle tip.

The catheter 13 is a flexible, long tube, the distal end of which can be implanted into the patient's central vein.

Thus, the port body 1, through the coordinated work of its various parts, realizes the functions of receiving, temporarily storing, and guiding the drug solution to the basic infusion function of the catheter 13. At the same time, it provides a sealed and controlled operating environment for the internal anti-plugging mechanism 2 and pushing mechanism 3.

B. Anti-Plugging Mechanism

The main function of the anti-plugging mechanism 2 is to convert the passive changes in the patient's body posture (gravitational potential energy changes) into active and precise mechanical cleaning actions, continuously stirring the liquid in the area of the catheter connector 15, preventing drug crystallization and adhesion. It mainly includes a movable component 21, a stirring component 22, and a damping component 23.

The movable component 21 is the power source of the anti-plugging mechanism, and its function is to sense the changes in the patient's body posture (i.e., the change in the direction of gravity) and convert them into its own mechanical displacement. In this embodiment, the movable component 21 is specifically a slidable ring 211.

The slidable ring 211 slides on the inclined inner wall of the reservoir chamber 12 by its own gravity, responding to changes in the direction of gravity with its positional changes. The slidable ring 211 is set inside the reservoir chamber 12. In order to obtain the maximum gravity response sensitivity, the slidable ring 211 is precision-machined from a high-density and biologically inert material, such as medical-grade titanium alloy or tungsten alloy. The slidable ring 211 has a ring-shaped structure, and its outer diameter is precision-calculated and processed to be sleeved on the outside of an internal structure (such as the fixed bush 231 of the damping component 23), with a small sliding fit gap maintained between the outer diameter of the slidable ring 211 and the cylindrical inner wall of the reservoir chamber 12. This relationship ensures that the slidable ring 211 can slide or tilt smoothly and without jamming along the axial direction of the cylindrical inner wall of the reservoir chamber 12, without excessive radial shaking due to an overly large gap, ensuring the stability and precision of the movement. When the patient is in an upright posture, the direction of gravity is parallel to the axis of the cylindrical inner wall of the reservoir chamber 12, and the slidable ring 211 will stably stay at the lowest position of the reservoir chamber 12 under its own gravity. When the patient's body undergoes postural changes such as leaning forward, backward, or lying on the side, the port body 1 tilts accordingly, causing the inner wall of the reservoir chamber 12 to also tilt relative to the direction of gravity. At this time, the center of gravity of the slidable ring 211 shifts relative to its support point on the inner wall of the reservoir chamber 12, and the component of gravity along the inner wall direction of the reservoir chamber 12 will drive the slidable ring 211 to overcome frictional force and fluid resistance, sliding towards the new lowest point of gravity. This seemingly simple sliding process precisely converts the macroscopic body posture change into a microscopic, predictable, and quantifiable mechanical displacement.

It is understandable that, in some embodiments, the movable component 21 is designed as one or more solid spheres, freely placed at the bottom of a specially designed reservoir chamber 12 with a bowl-shaped or V-shaped track. When the port body 1 tilts, the sphere will roll along the track to a new lowest point under the action of gravity. The rolling friction coefficient of the sphere is extremely low, and the response is very sensitive. By processing grooves or keyways on the sphere to engage with the corresponding structure of the stirring component, its rolling motion can be converted into a precise stirring action. This solution has high mechanical efficiency and can respond to very small angle changes.

It is understandable that, in some embodiments, the movable component 21 includes a micro-pivot structure set at the center of the inner wall at the top of the reservoir chamber 12, and a pendulum weight block made of high-density material, which is connected in rotation with the micro-pivot structure through a rigid connecting arm. When the port body 1 tilts, the pendulum weight block will swing around the micro-pivot structure like a pendulum, always pointing to the lowest point of gravity. The angular displacement generated by its swing can be converted into the required linear or reciprocating motion of the stirring component through a structure at the end of the connecting arm (such as a gear, connecting rod, etc.). This solution is compact in structure and is particularly suitable for the thinner design of intravenous ports with limited vertical space.

The stirring component 22 is mainly used to precisely transmit and convert the macroscopic mechanical displacement generated on the movable component 21 into microscopic physical stirring in the area of the catheter connector 15, which is most prone to blockage. Through actions such as stirring and scraping, it generates strong local vortices and shear forces near the catheter connector, actively and continuously flushing the inner wall of the port, preventing high-viscosity drug molecules from adhering, gathering, and crystallizing, thereby achieving the ultimate goal of preventing blockage. In this embodiment, the stirring component 22 specifically includes a rigid stirring rod 221 and an inclined panel 222 that provides support and guidance for it.

The stirring rod 221 is mainly used as a force transmitter and action executor. One of its ends receives displacement from the movable component 21, and the other end generates stirring at the catheter connector 15. To ensure effective force transmission and precise positioning, the stirring rod 221 is a rigid rod made of biocompatible material (such as medical-grade stainless steel or PEEK). Its first end is firmly fixed on the top surface of the movable component 21 (i.e., the slidable ring 211). Its shaft passes through a through hole provided in the inclined panel 222 at the bottom of the reservoir chamber 12. The length of its second end (i.e., the working end) is precisely designed so that it is always located at or slightly inside the entrance of the catheter connector 15.

The main functions of the inclined panel 222 are, on the one hand, its central channel provides guidance and support for the reciprocating motion of the stirring rod 221; on the other hand, its inclined plate surface design can utilize gravity to guide the liquid and drugs in the reservoir chamber 12 to naturally converge to the lowest point, the catheter connector 15, improving infusion efficiency. In this embodiment, the inclined panel 222 is a plate-like structure fixedly installed at the bottom of the reservoir chamber 12, and its surface is inclined towards the catheter connector 15. A precision-machined channel is opened in the center of the plate. A first sealing ring 2221 made of a medical-grade elastomer is installed on the inner wall of the channel. The inner diameter of this sealing ring 2221 is slightly smaller than the outer diameter of the stirring rod 221, forming an interference fit. When the movable component 21 (slidable ring 211) slides along the inner wall of the reservoir chamber 12 due to gravity, the stirring rod 221 fixed on it also moves accordingly. Due to the constraint of the central channel of the inclined panel 222, the composite motion (axial and radial) of the slidable ring 211 is decomposed and converted into a complete reciprocating stirring of the working end of the stirring rod 221 in the small space of the catheter connector 15. This stirring, although the stroke is very short, is sufficient to generate strong local vortices and shear forces at the microscopic level at the port opening. This micro-turbulence can effectively wash away any high-viscosity drug molecules attempting to adhere to the pipe wall, causing them to be re-suspended in the main flow, thus being unable to form crystal nuclei. At the same time, when the first sealing ring 2221 moves up and down on the stirring rod 221, its elastic deformation can closely fit its surface, forming a reliable dynamic seal, preventing liquid from leaking from the channel.

It is understandable that, in some embodiments, the working end of the stirring rod 221 is replaced with a micro flexible brush head made of biocompatible polymer material (such as nylon or silicone). When the moving component drives the stirring rod to move, the bristles of the brush can penetrate into the entrance edge of the catheter connector 15 to perform a "brushing-like" cleaning action, which can more effectively remove the already slightly adhered viscous residue. The softness of the bristles can also ensure that the inner wall of the catheter is not damaged during contact.

It is understandable that, in some embodiments, the working end of the stirring rod 221 is designed as one or a group of micro-scrapers with a specific angle, the shape of which is precisely conformal with the geometry around the catheter connector 15. When the stirring rod moves, the scraper can closely scrape against the surface of the connector edge, physically peeling off and removing adhered substances. The scraper can be designed to have a certain elasticity to provide continuous contact pressure while avoiding excessive wear.

The main function of the damping component 23 is to apply a damping force proportional to the velocity of the movement of the movable component 21. This ensures that regardless of whether the patient's body movements are slow and gentle or rapid and vigorous, the movement of the internal movable component 21 and stirring component 22 is always precisely controlled within a preset, smooth, and gentle velocity range. This function fundamentally ensures the absolute safety of the entire passive anti-plugging system, avoiding any potential risks that may be caused by excessively fast movement of internal components, such as drastic fluctuations in liquid pressure, blood return, and mechanical impact on tissues.

In this embodiment, the damping component 23 is specifically a single-stage pneumatic damper (or air shock absorber). It mainly includes a fixed bush 231 and a slidable annular compression component 232.

The main function of the fixed bush 231 is to act as a cylinder, providing a sealed space for the movement of the compression component 232. The fixed bush 231 is a ring-shaped sleeve, fixedly installed on the inner wall of the reservoir chamber 12. Its internal space forms a ring-shaped sealed air chamber 233. On the wall of the fixed bush 231, at least one (for example, four, uniformly distributed along the circumference) precisely controlled diameter through hole 235 is machined.

The main function of the compression component 232 is to act as a piston, generating a damping force by compressing or sucking air while sliding within the air chamber 233. The compression component 232 is a ring-shaped piston-like component; its shape is precisely matched with the inner shape of the air chamber 233. It is set inside the air chamber 233 and can slide freely in the axial direction. The compression component 232 is rigidly connected to the top of the movable component 21 (slidable ring 211) through a rigid connecting plate 234 to form a rigid whole. Therefore, any axial displacement of the slidable ring 211 will one-to-one drive the compression component 232 to produce the exact same displacement within the air chamber 233. Its outer peripheral surface and the inner peripheral surface of the air chamber 233 are in a sliding fit with a very small gap. The compression component 232 utilizes the Throttling Effect in fluid mechanics. When the movable component 21 moves rapidly, the rigidly connected compression component 232 will also move rapidly within the air chamber 233, thereby compressing the air on one side. Since the air chamber 233 is sealed, the compressed air cannot be discharged instantaneously and must be throttled through the narrow through holes. When the gas is forced to pass at high speed through a through hole with a cross-sectional area much smaller than the cross-sectional area of the air chamber, due to energy conversion, the flow velocity of the gas increases sharply while the pressure drops significantly. At the same time, strong vortices are formed at the exit of the hole, leading to significant energy dissipation. This energy dissipation macroscopically manifests as a huge resistance to the gas flow. This resistance acts back on the compression component 232, forming a strong damping force highly correlated with the movement speed of the compression component 232. The faster the movement, the greater the damping force. This damping force will effectively slow down the speed of the entire moving system, ensuring that even under a sudden action by the patient, the stirring motion of the internal stirring rod is always gentle and smooth. When the movement is in the opposite direction, the air chamber on the other side forms a negative pressure, and the external air is slowly sucked in through the through hole 235, producing the same damping effect.

It is understandable that, in some embodiments, the damping component 23 is designed as a sealed chamber filled with a high-viscosity, biocompatible liquid (such as medical-grade silicone oil). A part of the movable component 21 (such as a blade or piston) moves within this chamber. When this component moves in the viscous liquid, it will be subjected to a large resistance generated by the liquid's viscosity, which is proportional to the movement speed, thereby achieving a stable damping effect. This method is simple in structure and has good linearity of the damping force.

It is understandable that, in some embodiments, the damping component 23 is designed as a controllable friction device. For example, a friction block made of elastic material (such as silicone) is installed on the movable component 21, and it is made to slide on a surface with a specific roughness. By precisely designing the normal force of the friction block and the friction coefficient of the contact surface, a friction damping force of a basically constant magnitude can be provided. Alternatively, a more complex structure can be designed, for example, using centrifugal force, where, when the movable component rotates too fast, the thrown-out weight will press the brake pad, generating a stronger friction force.

It is understandable that, in some embodiments, the damping component 23 is designed as an elastomer damper, with buffer blocks made of high-damping elastomer (such as special rubber or gel) set at both ends of the movable component 21's movement track. When the movable component moves to the end of its stroke, it will contact and compress these buffer blocks. During the deformation and rebound process of the elastomer, most of the kinetic energy will be converted into heat through internal friction, thus playing a role in buffering and deceleration. This solution is mainly used for deceleration at the end of the stroke to prevent impact.

It is understandable that, in some embodiments, the damping component 23 is designed as a multi-stage damping system with multiple air chambers and through holes of different apertures. For example, a piston enters different air chambers at different stages of its movement, or through a variable throttle valve, the damping force can be non-linearly adjusted according to the position or velocity of the piston. This can achieve a more optimized velocity control curve, such as small initial movement resistance and a sharp increase in resistance at high speeds.

C. Pushing Mechanism

The pushing mechanism 3 is an optional enhancement module, and its main function is to provide a complementary and larger-range cleaning capability to the stirring component 22. When the stirring component 22 focuses on high-frequency, precise cleaning of the local area of the catheter connector 15, the pushing mechanism 3 is responsible for periodically sweeping and stirring the entire bottom of the reservoir chamber 12. It can effectively scrape and stir the boundary layer liquid at the bottom of the reservoir chamber, "lifting" the loose drug particles that may be deposited or attached here, so that they are suspended in the main flowing liquid, to be carried away by the vortex generated by the primary stirring system, or to be completely cleared during the next washing pipe. In this embodiment, the pushing mechanism 3 includes a movable displacement component 31, a grid plate 32 linked with it, and a connecting rod 35 connecting the displacement component and the grid plate 32.

The displacement component 31 is similar to the movable component 21; it is also a gravity-sensitive component used to capture gravity changes and convert them into displacement, providing driving force for the grid plate 32. In this embodiment, the displacement component 31 is specifically a displacement ring 311. The displacement ring 311 is a ring-shaped component set on the upper inner wall of the reservoir chamber 12. It is set inside an integrally formed or fixedly installed ring-shaped stopping structure 33. The inner surface of the stopping structure 33 forms a smooth guide surface. The outer wall of the displacement ring 311 is in sliding cooperation with the inner wall of the stopping structure 33, allowing it to slide up and down guided by the guide surface.

The grid plate 32 is mainly used for reciprocating sweeping actions at the bottom of the reservoir chamber 12. The grid plate 32 is located at the bottom of the reservoir chamber 12, closely adhering to the surface of the inclined panel 222. It is composed of a plurality of grid strips 321 that are parallel to and spaced from each other, like a miniature plow. The extension direction of these grid strips 321 is designed to be perpendicular to the main moving direction of the displacement ring 311 to achieve the maximum stirring effect.

It is understandable that, in some embodiments, the grid plate 32 is replaced with a whole piece of flexible scraper made of medical-grade silicone or similar elastic material. The edge shape of the scraper completely matches the bottom contour of the reservoir chamber 12. When driven, the scraper can sweep like a car wiper, closely against the bottom surface, more thoroughly removing adhered substances, cleaning without dead corners.

It is understandable that, in some embodiments, the grid plate 32 is replaced with a cylindrical cleaning roller that can roll at the bottom of the reservoir chamber 12. The surface of the cleaning roller can be designed with textures, grooves, or wrapped with adsorbent material. When driven, it will roll back and forth at the bottom, cleaning the bottom by means of rolling and friction.

The main function of the connecting rod 35 is to transmit the macroscopic displacement generated by the displacement component 31 (displacement ring 311) due to gravity changes to the grid plate 32 at the bottom, without distortion and one-to-one. Its rigid nature is the key to realizing this function. It ensures that during the process of transmitting pushing and pulling forces, the connecting rod itself will not bend, compress, or stretch, thus ensuring that the movement stroke of the grid plate 32 is completely synchronized with the movement stroke of the displacement ring 311, achieving precise mechanical linkage. In addition, the connecting rod 35 also plays a structural support role, ensuring that the grid plate 32 always maintains a fixed relative position and posture with the displacement ring 311. To meet the requirements of long-term implantation in the human body and withstand repeated movements, the material of the connecting rod 35 must be non-toxic, non-irritating, and non-sensitizing to human tissues. The material needs to have sufficient Young's modulus and yield strength so that it does not deform when subjected to fluid resistance. The material also needs to be able to resist the chemical corrosion of physiological saline, drug solutions, and body fluids for a long time. The material also needs to reduce its own weight as much as possible to reduce the inertia of the entire moving system and improve its response sensitivity to gravity changes. And it must be able to withstand tens of thousands or even hundreds of thousands of reciprocating movements over several years without fatigue fracture. Materials can be selected, for example, from medical-grade titanium alloy (such as Ti-6Al-4V ELI), high-performance medical polymers (such as PEEK, polyetheretherketone), and medical-grade stainless steel (such as 316LVM), but are not limited to these. The grid plate 32 is connected to the bottom of the upper displacement ring 311 through one or more slender, highly polished connecting rods 35. On the premise of ensuring sufficient buckling strength, the diameter of the connecting rod 35 is designed to be as small as possible to reduce its resistance to movement in the fluid and to reduce the size of the sealing structure (second sealing ring 34) it passes through. The rigid structure ensures the most direct and efficient linear force transmission. A highly polished surface has an extremely low surface roughness (Ra) value, which is crucial for reducing the dynamic friction with the second sealing ring 34, preventing wear, and inhibiting the adhesion of bacterial biofilms. The two ends of the connecting rod 35 can be designed with threaded, snap-fit structures, or form a permanent connection through laser welding, interference fit, etc., according to the connection method with the displacement ring 311 and the grid plate 32. One end is fixedly connected to the bottom of the displacement ring 311, and the other end is fixedly connected to the top of the grid plate 32. Its shaft passes vertically through the stopping structure 33 set in the middle of the reservoir chamber and forms a dynamic sealing fit with the second sealing ring 34 at the passage. This layout ensures the stability and guidance of its movement path. To ensure sealing, a groove is opened on the inner wall of the stopping structure 33, and a second sealing ring 34 is installed in it. This sealing ring forms a reliable dynamic seal with the outer surface of the connecting rod 35. When the patient's body posture changes and the direction of the gravity field changes, the upper displacement ring 311 slides precisely along the track defined by its stopping structure 33 due to its own weight. Since the connecting rod 35 is firmly fixed on the displacement ring 311, any displacement of the displacement ring 311 will be 100% and, without delay, transmitted to the connecting rod 35. The connecting rod 35 moves down synchronously by the exact same distance, thereby driving its lower end, the grid plate 32, to complete the cleaning action. The multiple grid strips 321 of the grid plate 32 can effectively scrape and stir the liquid at the bottom, lifting the sediment. When the patient returns to the original posture, the displacement ring 311 returns to its initial position under the action of gravity, driving the grid plate 32 to move in the opposite direction, completing one cleaning cycle.

In this embodiment, passive self-cleaning is achieved through a cyclical mechanical cycle driven by changes in the patient's body posture. Taking a typical "stoop-arise" action as an example to illustrate its complete working process and principle: when the patient is in an upright or sitting posture, the main axis of the port body 1 is parallel to the direction of gravity. In this gravitational field, all gravity-sensitive moving parts are in their designed initial rest position. The movable component 21 (slidable ring 211), under its own gravity, stably rests at the lowest point of the reservoir chamber 12. The connected stirring rod 221 and compression component 232 are also at their lowest positions. The displacement ring 311 of the optional pushing mechanism 3 is also at the lowest point of its track, and the grid plate 32 is at one end of its stroke. The entire system is in a stable equilibrium state of minimum energy, waiting for the next trigger. When the patient leans forward and performs a stooping action, the port body 1 implanted under their skin also tilts accordingly, and its main axis forms an angle with the direction of gravity. The tilting of the port body 1 breaks the original force balance. Gravity will drive the movable component 21 (slidable ring 211) to slide along the inclined inner wall of the reservoir chamber 12 to a new lowest point of gravity. The displacement of the slidable ring 211, through the rigid connection, drives the stirring rod 221 to perform a complete reciprocating stirring near the catheter connector 15. This action generates strong vortices and shear forces at the microscopic level, effectively flushing the inner wall of the connector and stripping off potentially adhered drug molecules. At the same time, the upper displacement ring 311 also slides along its track due to gravity, and through the connecting rod 35, it drives the bottom grid plate 32 to perform a large-scale sweep at the bottom of the reservoir chamber 12, lifting the deposited drug particles at the bottom. While all the above movements are occurring, the compression component 232 linked with the slidable ring 211 moves within the air chamber 233, compressing the air. The compressed air must be slowly discharged through the narrow through hole 235. This throttling process produces a large damping force, which acts back on the entire moving system, effectively slowing down the moving speed of the slidable ring 211. This ensures that even if the patient's stooping action is very fast, the cleaning actions of the internal stirring rod and the grid plate are always smooth and gentle. When the patient returns from a stooping posture to an upright posture, or changes to a lying flat posture, the orientation of the port body 1 relative to the direction of gravity changes again. The new gravitational field direction will drive the movable component 21 (slidable ring 211) from the position it moved to due to stooping, to slide again to the lowest point relative to the current direction of gravity (which is usually its initial position in the upright state). During this recovery process, the stirring rod 221 will perform an stirring action in the opposite direction to when stooping, cleaning the catheter connector 15 area again. Similarly, the grid plate 32 will also sweep in the opposite direction, completing a full cleaning cycle. The compression component 232 moves in the opposite direction within the air chamber, causing a pressure change on the other side of the air chamber. The air slowly flows in or out through the hole 235, which also produces a stable damping effect on the recovery motion, preventing it from hitting the bottom of the reservoir chamber due to rapid recovery, protecting the integrity of the internal structure. Through such repeated cycles of "stoop-stir-slowdown" and "recover-stir-slow-down," this intravenous port can, during each posture change of the patient, complete a dual, controlled self-cleaning of the catheter connector and the bottom of the reservoir chamber, thereby achieving a continuous and reliable anti-plugging effect.

Thus, this embodiment, by integrating a purely mechanical, gravity-driven passive anti-plugging mechanism inside an implantable intravenous port, achieves the following significant technical effects:

Realizes preventive maintenance: This embodiment is not about remedying after a blockage occurs, but rather, after each infusion, it utilizes the patient's daily activities to continuously perform microscopic cleaning, eliminating the formation conditions for the core of drug crystals at the source, nipping the risk of blockage in the bud.

Can operate safely and unnoticeably: The overall design of this embodiment is purely mechanical and passive, requiring no batteries, motors, circuits, or external control units, completely avoiding all known risks that may be brought by long-term implantation of electronic devices in the body, such as battery depletion, circuit failure, and electromagnetic compatibility issues. The key damping component ensures that its internal movement is always smooth and gentle, without any physiological interference to the patient, achieving a completely unnoticeable and safe operation.

Highly reliable and durable: The structure of this embodiment is simple, with few moving parts, and all components are made of medical-grade materials with high biocompatibility and wear resistance (such as titanium alloy, PEEK, etc.). This ensures that the device can continuously, stably, and reliably exert its anti-plugging function during an implantation period of several years, having extremely high long-term reliability.

Realizes automatic conversion of daily body movements into cleaning actions: This design cleverly converts the patient's unavoidable, macroscopic, and irregular daily body movements into microscopic, precise, and safely buffered cleaning actions. This clever use of "biological energy" allows the anti-plugging function to be performed around the clock, automatically, without any extra operations from the patient or medical staff, greatly reducing the patient's nursing burden and psychological stress, and improving their quality of life.

In summary, this implantable intravenous port with a passive anti-plugging mechanism, through a clever and completely self-sufficient mechanical system, successfully solves the long-standing clinical problem of catheter blockage, providing a safer, more reliable, and more worry-free solution for patients requiring long-term intravenP-701US-2500034ous therapy, and has significant clinical value and economic benefits.

The embodiments described above are merely examples of the present disclosure, and should not be used to limit the scope of the present disclosure, which may have various modifications and variations made by specialists in the field. Any modification, equivalent replacement or improvement made within the spirits and principles of the present disclosure shall be included in the scope of protection of the present disclosure.

What is claimed is:

1. An implantable intravenous port with a passive anti-plugging mechanism, comprising:

a port body, wherein the port body internally forms a reservoir chamber and a catheter connector in communication with the reservoir chamber; and an anti-plugging mechanism set inside the reservoir chamber, the anti-plugging mechanism comprising a movable component, a stirring component, and a damping component;

wherein the movable component is capable of moving within the reservoir chamber in response to gravity;

wherein one end of the stirring component is connected to the movable component, and the other end extends to the vicinity of the catheter connector; and wherein the damping component comprises a fixed bush and a compression component, the fixed bush is fixedly set on an inner wall of the reservoir chamber and internally forms an air chamber, the compression component is slidably set within the air chamber, and a wall of the fixed bush is provided with a through hole, the through hole communicating with both sides of the air chamber.

2. The implantable intravenous port according to claim 1, wherein the movable component comprises a slidable ring slidably set on an inner wall of the reservoir chamber, the slidable ring being sleeved on and slidably connected to the inner wall of the reservoir chamber; and wherein the stirring component comprises a stirring rod, and one end of the stirring rod is fixedly connected to the slidable ring.

3. The implantable intravenous port according to claim 2, wherein a bottom of the reservoir chamber is fixedly provided with an inclined panel, the inclined panel is provided with a channel, the stirring rod passes through the channel, and a first sealing ring is provided at the channel, the first sealing ring forming a dynamic seal between the stirring rod and the channel.

4. The implantable intravenous port according to claim 1, wherein the damping component further comprises a connecting plate, one end of which is connected to the movable component, and the other end is connected to the compression component.

5. The implantable intravenous port according to claim 1, further comprising a pushing mechanism, wherein the pushing mechanism is set inside the reservoir chamber and acts on a bottom region thereof, the pushing mechanism comprising a movable displacement component and a grid plate connected to the displacement component.

6. The implantable intravenous port according to claim 5, wherein the displacement component comprises a displacement ring, the displacement ring is slidably set on an inner wall of the reservoir chamber, and the grid plate is in linkage with the displacement ring.

7. The implantable intravenous port according to claim 6, wherein the inner wall of the reservoir chamber is provided with a stopping structure, the stopping structure is for guiding the sliding of the displacement ring, and a second sealing ring is provided within the stopping structure.

8. The implantable intravenous port according to claim 1, wherein a top of the port body is provided with a silicone film, a catheter is connected at the catheter connector, and the catheter is fixed to the port body by a positioning sheath.

9. The implantable intravenous port according to claim 1, wherein the number of the through holes is a plurality, and the plurality of through holes are uniformly distributed along a circumferential direction of the fixed bush; and wherein an outer peripheral surface of the compression component and an inner peripheral surface of the air chamber are in a sliding fit.

10. The implantable intravenous port according to claim 5, wherein the grid plate comprises a plurality of grid strips, the plurality of grid strips are set parallel to and spaced from each other, and an extension direction of the grid strips is perpendicular to a moving direction of the displacement component.

* * * * *